US012805964B2

(12) United States Patent
Bailey et al.

(10) Patent No.: US 12,805,964 B2
(45) Date of Patent: Nov. 24, 2026

(54) AUTOCLAVE SELF-DESTRUCTING MEDICAL DEVICES

(71) Applicant: Mainstream Medical Devices, LLC, Austin, TX (US)

(72) Inventors: Aaron M Bailey, Austin, TX (US); Dana M Wilcox, Austin, TX (US)

(73) Assignee: Mainstream Medical Devices, Austin, TX (US)

( * ) Notice: Subject to any disclaimer, the term of this patent is extended or adjusted under 35 U.S.C. 154(b) by 1136 days.

(21) Appl. No.: 17/842,470

(22) Filed: Jun. 16, 2022

(65) Prior Publication Data

US 2023/0000582 A1 Jan. 5, 2023

Related U.S. Application Data

(60) Provisional application No. 63/217,546, filed on Jul. 1, 2021.

(51) Int. Cl.

| | |
|---|---|
| ***A61L 2/08*** | (2026.01) |
| ***A61B 17/00*** | (2006.01) |
| ***A61B 17/16*** | (2006.01) |
| ***A61B 17/20*** | (2006.01) |
| ***A61B 17/32*** | (2006.01) |
| ***A61B 90/00*** | (2016.01) |
| ***A61L 2/06*** | (2006.01) |
| ***A61L 2/28*** | (2006.01) |
| *A61B 17/3211* | (2006.01) |
| *A61L 103/15* | (2026.01) |

(52) U.S. Cl.
CPC .......... *A61B 90/08* (2016.02); *A61B 17/1604* (2013.01); *A61L 2/06* (2013.01); *A61L 2/28* (2013.01); *A61B 2017/32113* (2013.01); *A61B 2090/0814* (2016.02); *A61L 2103/15* (2026.01)

(58) Field of Classification Search
CPC ............ A61B 2090/0814; A61B 90/08; A61B 2017/32113; A61B 17/1604; A61L 2202/24; A61L 2/06; A61L 2/28
USPC ........ 422/26, 307; 604/22; 606/80, 167, 169
See application file for complete search history.

(56) References Cited

U.S. PATENT DOCUMENTS 5,810,859 A * 9/1998 DiMatteo ....... A61B 17/320068 606/169

* cited by examiner

*Primary Examiner* — Monzer R Chorbaji
(74) *Attorney, Agent, or Firm* — FisherBroyles LLP; Russell Manning

(57) ABSTRACT

Single use medical devices that incorporate one or more destruct elements configured to deform during an autoclave cycle, rendering the device visually damaged or unusable. The use of such destruct elements prevents reuse (knowingly or unwittingly) of single use devices on patients after off-label autoclaving.

5 Claims, 9 Drawing Sheets

AUTOCLAVE SELF-DESTRUCTING MEDICAL DEVICES

CROSS REFERENCE

The present application claims the benefit of the filing date of U.S. Provisional Patent Application No. 63/217,546 having a filing date of Jul. 1, 2021, the entire contents of which is incorporated herein by reference.

FIELD

The present disclosure is directed to single-use medical devices and implements (hereafter "devices"). More specifically, the present disclosure is directed to single-use medical devices that, when subjected to autoclave processing for potential reuse, deform, destruct and/or provide a visual indication that the devices are not reusable.

BACKGROUND

Historically, medical devices, such as those utilized in surgery (e.g., scalpels, forceps, spreaders, scrapers, etc.) were reusable. That is, the devices were intended to be re-sterilized/decontaminated and reused after a medical procedure. Such re-sterilization has advanced over time from simply immersing the devices or tools in alcohol to the current practice of autoclave sterilization. In the latter regard, medical devices are inserted into an autoclave chamber where they are subjected to elevated temperatures, pressures and, commonly, steam. By way of example, many autoclaves used for sterilizing medical devices subject those devices to pressurized saturated steam at approximately 121° C. (250° F.) for around 15-20 minutes depending on the size of the load and the contents.

While autoclave sterilization is an industry accepted means for cleaning reusable medical devices, the process is not always one-hundred percent effective. That is, in some cases bacteria, pathogens or other contaminants survive the autoclave process. This is more common for devices that have internal passageways where such contaminants may be partially protected during the autoclave process. The inability to fully sterilize reusable devices can result in infection risks, when utilized with subsequent patients. Accordingly, there has been an ongoing shift in the medical field to single-use medical devices. Such devices are designed to be utilized once in a hospital or clinic and then disposed. In this regard, single-use devices are often delivered in sterilized packages, which are opened shortly before or during a medical procedure. In such an arrangement, no sterilization is required before use. Such single-use devices are intended to eliminate re-sterilization problems sometimes encountered by reusable medical devices. To ensure the single-use devices are not reused, manufacturers often put a single-use labels and warnings on the packaging and/or ISO symbols on the medical device itself alerting medical professionals that the device should be disposed after use.

BRIEF SUMMARY OF THE DISCLOSURE

The present inventor(s) has recognized that many single use devices (SUDs) are erroneously reused. By way of example, during surgery, it is common for all devices or tools used during surgery be placed in a bucket or tray after use. In many instances, reusable devices and SUDs may be comingled. If SUDs are comingled with reusable devices, the SUDs may be erroneously re-sterilized in an autoclave and reused. Further, SUDs may be purposely re-sterilized as a cost saving measure. However, as SUDs are not designed for reuse, operating parts of re-sterilized SUDS can be dull, loose, bent or otherwise out of calibration after autoclaving. The presented systems and methods prevent such unintentional or other off-label reuse of SUDS on patients.

In an arrangement, a destruct element (e.g., thermally deformable element) is incorporated into a SUD that deforms during autoclaving. Most commonly, at least a portion of the destruct element has a melting point below an autoclaving process temperature. That is, the destruct element has a low melting point of less than about 250° F., less than about 230° F. or even less than about 180° F. When subjected to autoclave processing temperatures, the destruct element deforms. Such deformation may provide a visual and/or tactile indication that the device is damaged and not intended for reuse. Size shape and color of the destruct element may be chosen to improve visual discernability. In some arrangements, deformation of the destruct element may prevent operation of a functioning or moving component(s) of the SUD. In any arrangement, a subsequent user of the device has in indication that the SUD has been unintentionally autoclaved in an off-label attempt to sterilize the SUD and that the SUD should not be utilized with a patient.

In an embodiment, a destruct element is disposed on a handle of a SUD. In such an embodiment, the destruct element may provide a visual or tactile indication that the SUD has improperly been exposed to an autoclave process.

In an embodiment, one or more destruct elements form or are disposed against a moving element of a SUD. Such SUDS may include, without limitation, retractable surgical knives and swiveling awls. In such embodiments, the destruct element(s) may prevent ordinary movement of the SUD once the SUD has been exposed to an autoclave process.

The foregoing and other aspects, features, details, utilities, and advantages of the present disclosure will be apparent from reading the following description and claims, and from reviewing the accompanying drawings.

DETAILED DESCRIPTION

Reference will now be made to the accompanying drawings, which at least assist in illustrating the various pertinent features of the presented inventions. The following description is presented for purposes of illustration and description and is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.

Broadly, the present disclosure is directed to single-use medical devices (SUDS) that are configured to deform (e.g., destruct) if re-sterilized in an autoclave process. Generally, each SUD includes a destruct element (e.g., thermally deformable element) that deforms in response to elevated temperatures present during autoclaving. Typically, at least a portion of the destruct element is formed of a material having a melting point below an autoclaving process temperature. That is, at least a portion the destruct element is made of a material having a melting point of less than about 250° F., less than about 230° F. or even less than about 180° F. When subjected to elevated temperature, during an autoclave processing, the destruct element deforms. Preferably, the destruct element grossly deforms. In this regard, materials having a melting point that is significantly less than the autoclaving temperature (e.g., at least 20° F.) may be preferred. However, this is not a requirement. Such deformation may provide a visual indication that the device is damaged and should not be used with a patient. In some arrangements, such deformation may prevent operation of a functioning or moving component(s) of the SUD. In any arrangement, a subsequent user of the device has an indication that the SUD has been unintentionally autoclaved in an off-label attempt to sterilize the SUD and that the SUD should not be utilized with a patient.

Figure 1A:
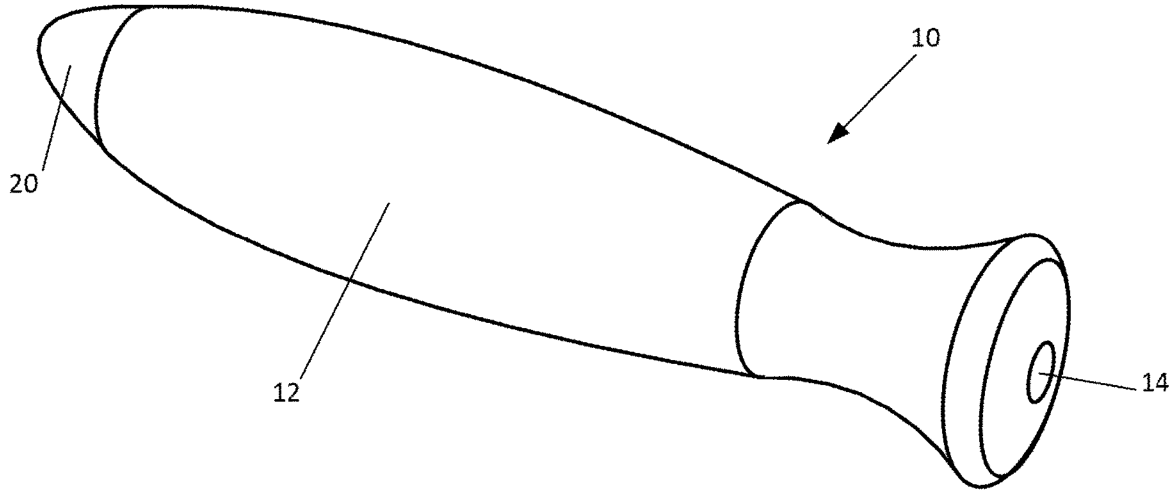
FIGS. 1A and 1B illustrate perspective and exploded perspective views, respectively of a single use medical device with a destruct element in accordance with the present disclosure.
Figure 1B:
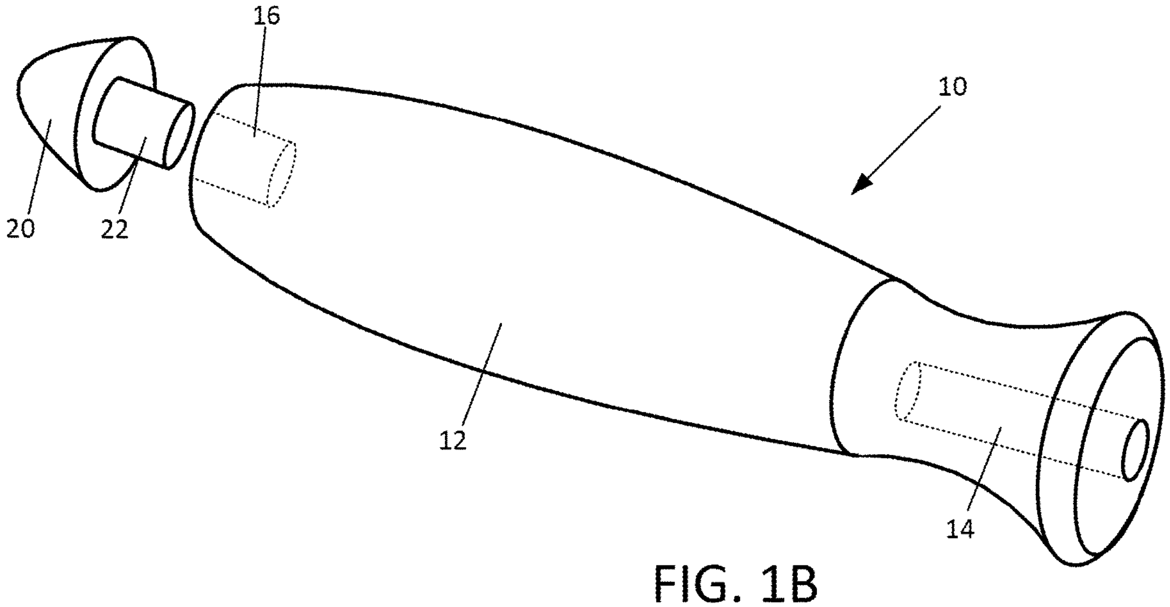

FIGS. 1A and 1B illustrate perspective and exploded perspective views, respectively, of one embodiment of a handle 12 of a single use medical device or SUD 10 that includes a destruct element 20. The illustrated SUD 10 does not include a medical implement which may be inserted within a cylindrical recess/aperture 14 formed within a forward/distal end of the handle 12 or otherwise attached to the handle. As will be appreciated, such a handle 12 could be utilized to support a variety of medical implements including, without limitation, retractors, scrapers, etc. Further, the handles of various differently configured SUDS provide a convenient location for incorporating a destruct element as discussed herein. Though presented in an embodiment as incorporating a destruct element on or within a handle of a SUD, the present disclosure is not limited to this location and destruct elements may be incorporated on other portions of a SUD. In the illustrated embodiment, the handle 12 includes a cylindrical recess 16 formed within its rearward/proximal end. In this embodiment, the destruct element 20 is formed with a mating cylindrical end 22 that fits within the cylindrical recess 16. When attached to the handle 12, the destruct element 20 may form a smooth uniform cap (e.g., generally hemispherical, domed, cylindrical, etc.) on the rearward end of the handle 12.

Figure 2A:
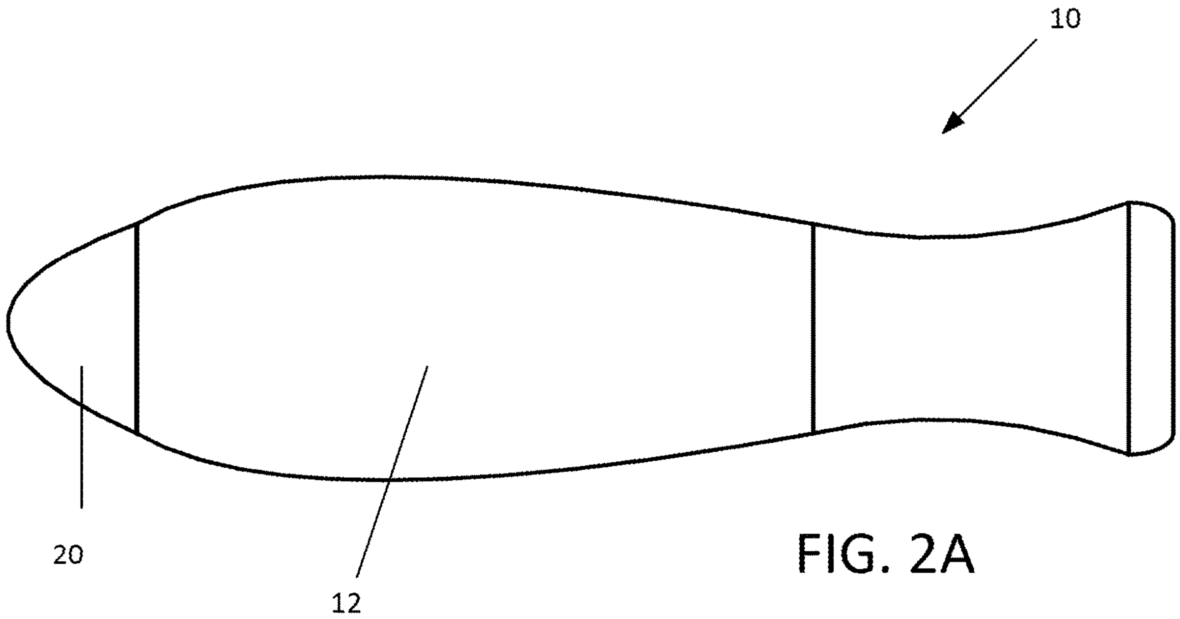
FIGS. 2A and 2B illustrate side views of the single use medical device of FIGS. 1A and 1B before and after an autoclaving process.
Figure 2B:
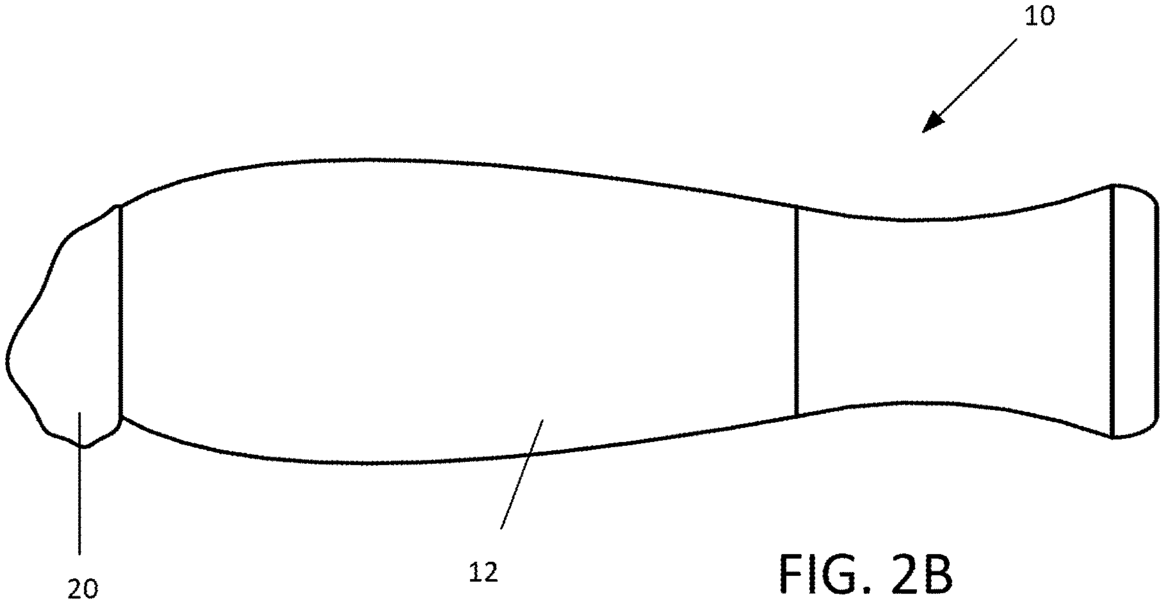

FIGS. 2A and 2B illustrate side views of the handle 12 before and after autoclaving, respectively. As illustrated in FIG. 2A, prior to autoclaving, the destruct element 20 may have a uniform shape on the proximal end of the handle 12. FIG. 2B illustrates a deformed destruct element 20 on the proximal end of the handle 1. That is, FIG. 2B illustrates the destruct element 20 after an elevated temperature is applied during an autoclaving process. As illustrated, the destruct element 20 at least partially deforms when exposed to temperatures above its melting point. In contrast, the handle 12 may be formed of a material having a melting point above autoclaving temperatures. Accordingly, the handle 12 may not experience deformation during the autoclaving process. Likewise, a medical implement attached to the handle (e.g., a metallic implement) would not experience deformation during the autoclaving process. However, due to the deformation of the destruct element 20, a subsequent user of the SUD 10 would have at least a visual indication that the SUD 10 is damaged and should not be re-used.

Figure 3A:
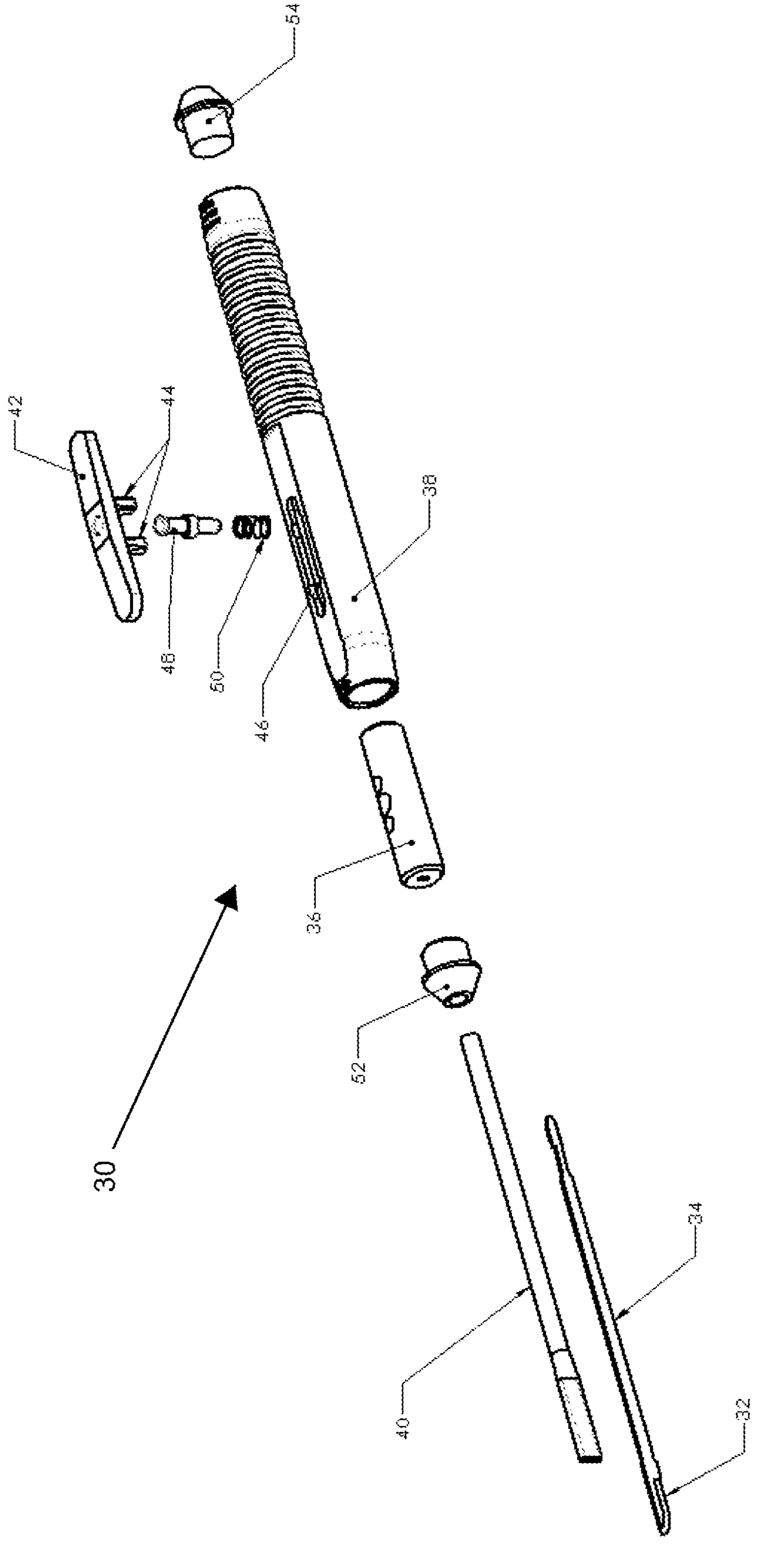
FIG. 3A illustrates a perspective view of another single use medical device with a destruct element in accordance with the present disclosure.

FIG. 3A illustrates an exploded perspective view of an exemplary single-use retractable surgical knife 30. The retractable surgical knife 30 is a SUD that incorporates one or more destruct elements. In the illustrated embodiment, one or more destruct elements may prevent movement of a component of the SUD after exposure to autoclaving temperatures. As illustrated, the knife 30 includes a blade 32 attached to a distal end of a blade shaft 34. The rearward/proximal end of the blade shaft 34 connects to a slider 36, which can slide linearly within an interior of a handle 38 of the knife 30. When assembled, the blade shaft 34 is disposed within the interior of a hollow shaft 40, which connects to a distal end of the handle 38. Advancement of the slider 36 toward the forward or distal end of the handle 38 advances the blade shaft 34 such that blade 32 extends beyond the distal end of the hollow shaft 40. Likewise, retraction of the slider 36 toward the rearward or proximal end of the handle 38 retracts the blade shaft 34 such that the blade 32 is disposed within an interior of the hollow shaft 40.

Figure 3B:
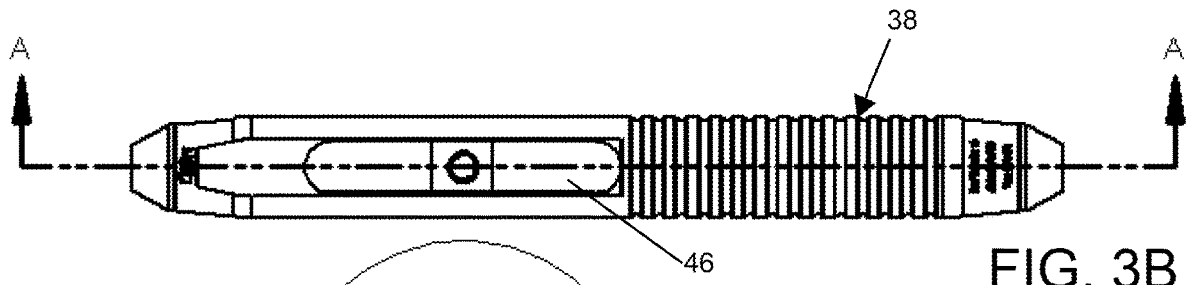
FIG. 3B illustrates a top view of a handle of the single use medical device of FIG. 3A.
Figure 3C:
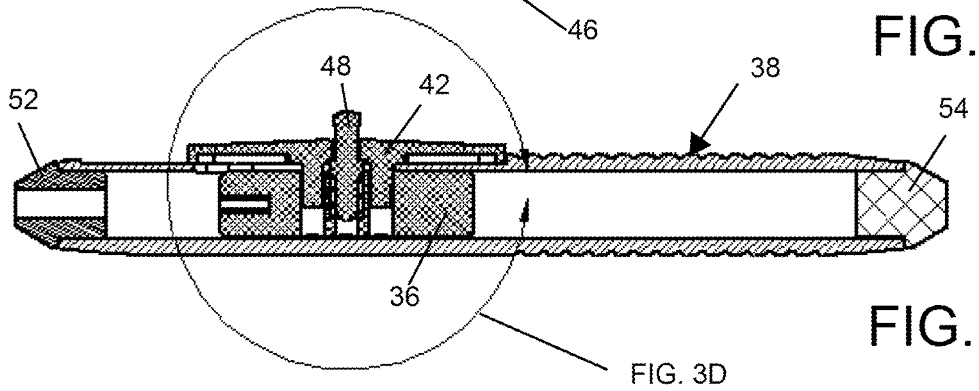
FIG. 3C illustrates a cross-sectional view of the handle of FIG. 3B.
Figure 3D:
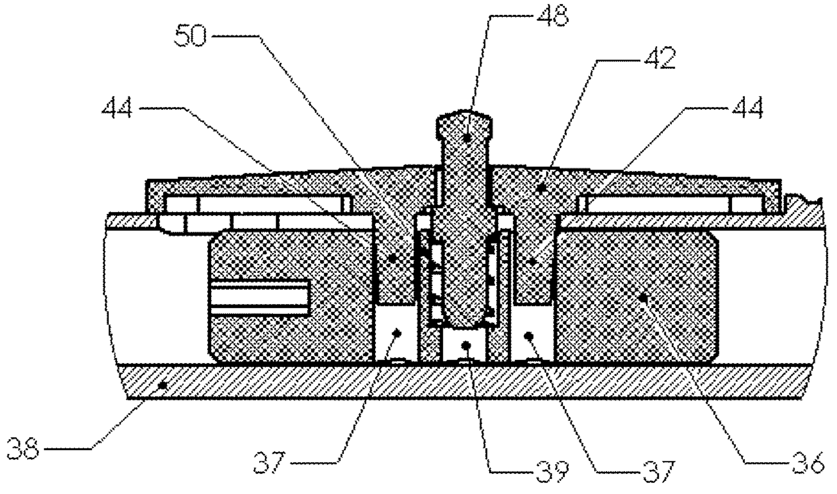
FIG. 3D illustrates a close-up cross-sectional view of an actuator assembly of the single use medical device of FIG. 3A.

FIGS. 3B and 3C illustrates a top view of the handle 38 and a cross-sectional view of the handle taken along a centerline plane A-A' of the handle, respectively. FIG. 3D illustrates an expanded view of a portion of FIG. 3C. As variously illustrated in FIGS. 3A-3D, a thumb actuator 42 connects to the slider 36, when the slider 36 is disposed within the interior of the handle 38. A user can manipulate the thumb actuator 42 to advance or retract the slider 36 and thereby advance or retract the blade 32. In the illustrated embodiment, studs 44 on the bottom of the thumb actuator 42 extend through a slot 46 in a sidewall of the handle 38 to engage the slider 36. More specifically, the studs 44 extend through the slot and engage mating openings 37 formed into the sider 36. In addition, a biasing pin 48 has a lower end disposed in an opening 39 in the slider 36 and an upper end that engages a bottom surface of the thumb actuator 42. A spring 50 is disposed in the opening 39 below a central collar of the biasing pin 48 and a lower end of the opening in the slider. Collectively, the biasing pin 48 and spring 50 require a user to depress the thumb actuator 42 prior to advancing or retracting the slider 36. However, it will be appreciated that a simple friction slider could be utilized. In addition to the above-noted components, the exemplary knife also includes a distal ferrule 52 on a forward end of the handle 38, which connects the hollow shaft 40 to the handle 38, and a rearward ferrule or cap 54 one a rearward end of the handle 38.

In the illustrated embodiment of the retractable surgical knife 30, various components may be thermally deformable elements (e.g., destruct elements). For instance, the slider 36, thumb actuator 42 and/or the biasing pin 48 may be formed of a material having a low melting point (e.g., below an autoclaving temperature). Accordingly, when subjected to elevated temperatures during autoclaving that exceed the melting point of these component, the components may deform. In the case of the slider 36, thumb actuator 42 and biasing pin 48, such deformation may prevent operation of the retractable knife 30. That is, such deformation may prevent the advancement and retraction of the blade 32 rendering the retractable knife 30 inoperable. For instance, the slider 36 may be a thermally deformable element that may melt to and, for example, adhere to the interior of the handle 38 preventing movement of the blade 32 once the slider 36 has re-solidified (e.g., after cooling). Likewise, additional thermally deformable components may melt and adhere to adjacent components. For instance, the actuator 42 may melt and adhere to the handle 38 and the biasing pin 48 may melt into and adhere with the spring 50. Stated otherwise, one or more components may at least partially melt together and/or adhere to adjacent components preventing subsequent movement. In addition, the knife 30 may include one or more destruct elements that provide a visual indication that the knife has been re-sterilized. For instance, the distal ferrule 52 and/or the proximal ferrule/cap 54 may be formed of a low melting point material that deform during an autoclaving process like the destruct element discussed in FIG. 2B.

Figure 4A:
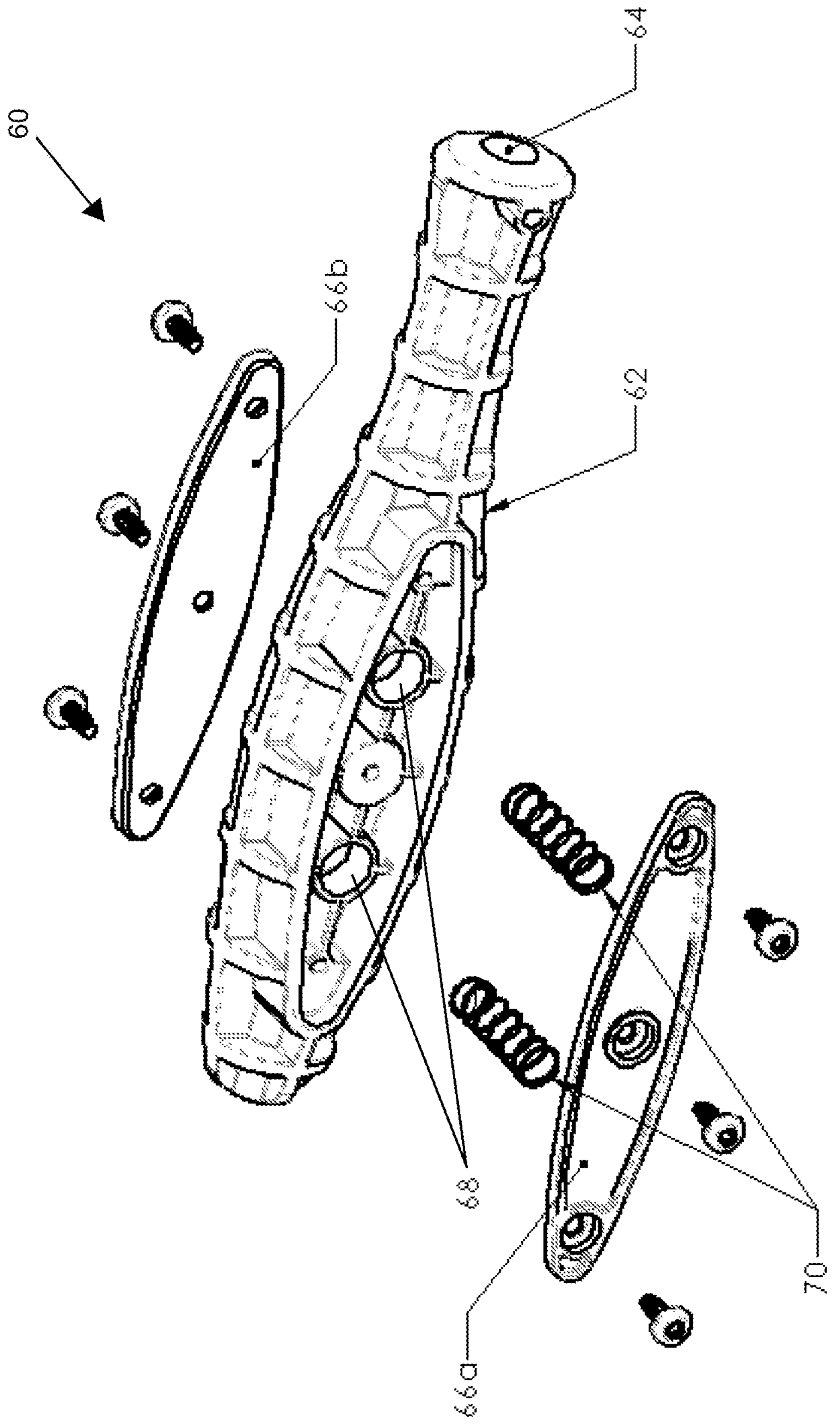
FIG. 4A illustrates another single use medical device with a destruct element in accordance with the present disclosure.
Figure 4B:
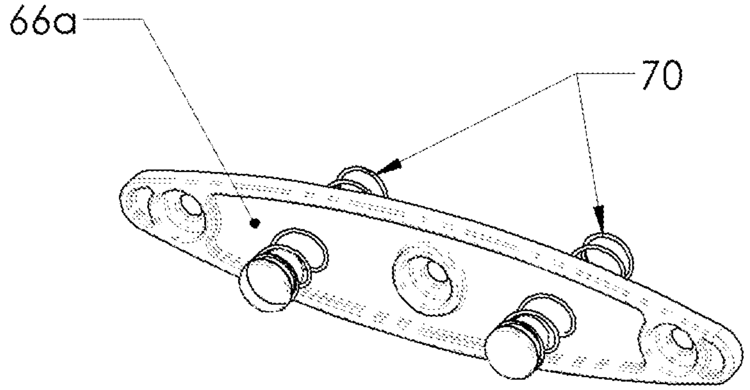
FIG. 4B illustrates the destruct element of the device of FIG. 4A after autoclaving.

FIGS. 4A and 4B illustrate another embodiment of a handle 62 of a SUD 60, which may support any of a variety of medical implements. As above, such a medical implement may be inserted within a cylindrical recess/aperture 64 formed within a forward or distal end of the handle 62 or otherwise attached to the handle. In this embodiment, the SUD 60 includes two side plates 66*a*, 66*b* (hereafter 66 unless specifically referenced), which are destruct elements. The plates 66 are formed of a material having a low melting point (e.g., below an autoclaving temperature). As illustrated, the side plates 66 may be attached to the handle 62 utilizing, for example, screws. However, other fasteners may be utilized. To ensure that the side plates 66 (e.g., destruct elements) deform during an autoclaving process, one or more biasing elements 70 (e.g., springs) are secured below the plates 66, when the plates are attached to the handle 62. As illustrated, the biasing elements 70 are coil springs (e.g., compression springs). However, other biasing elements may be utilized (leaf springs, torsion springs, elastomeric blocks, etc.). The biasing elements are partially disposed within recessed openings 68 formed in the handle 62. The biasing elements 70 are compressed when the plates 66 are attached to the handle (not shown). The biasing elements 70 apply an expansive force between the handle 62 and a bottom surface of the plate 66, when the plate is affixed to the handle 62. Prior to experiencing elevated temperatures, the side plates 66 have sufficient rigidity to maintain compression of the biasing elements 70. Once exposed to elevated temperatures during autoclaving (e.g., temperatures above the melting point of the plates 66), the biasing elements 70 may deform the plates 66 (e.g., destruct elements) or even protrude through the surface of the plates 66 as illustrated in FIG. 4B. In either arrangement, a user grasping the handle 62 will have a tactile indication as well as a visual indication that the SUD 60 should not be utilized.

Figure 5A:
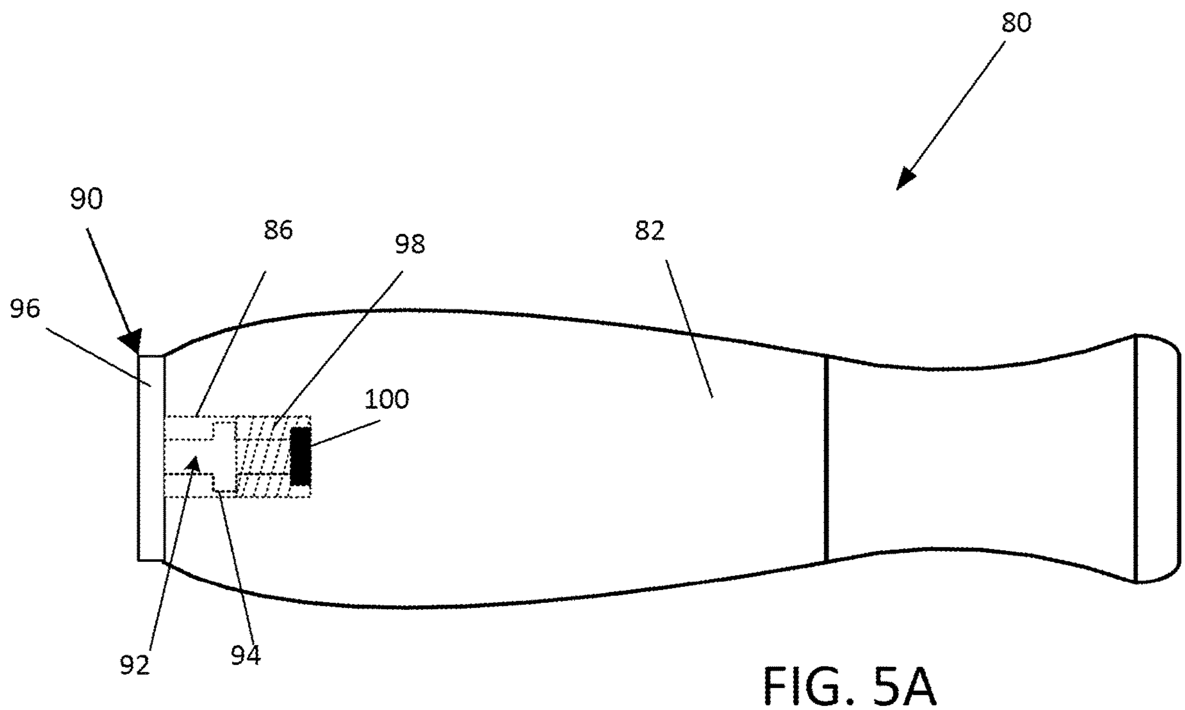
FIGS. 5A and 5B illustrate another single use medical device with a destruct element in accordance with the present disclosure.
Figure 5B:
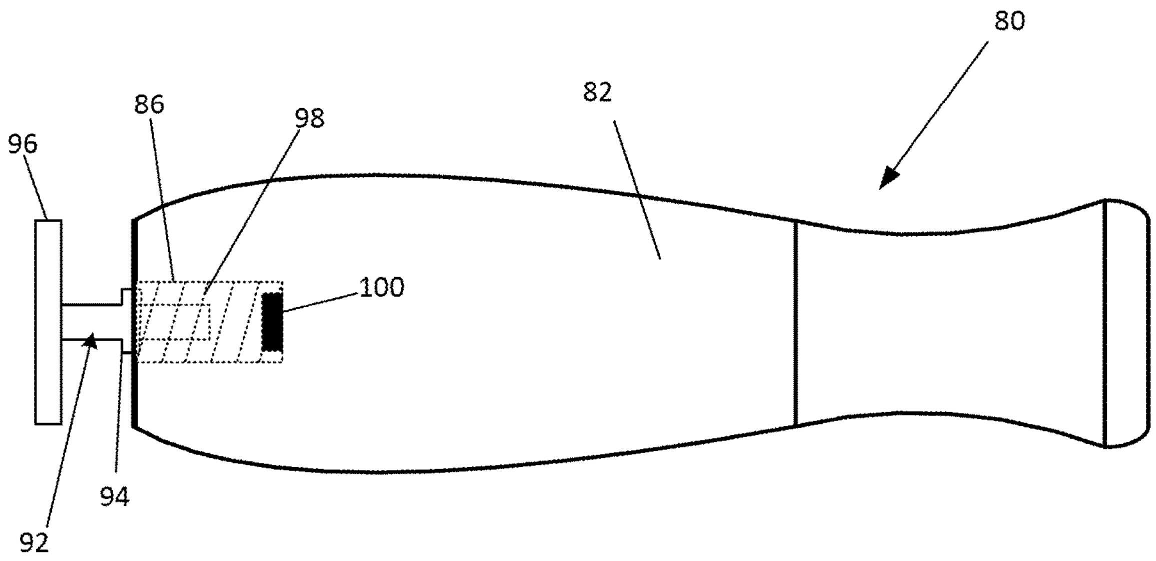

Though discussed above as utilizing a destruct element that deforms in response to elevated temperatures, it will be appreciated that the destruct element may be any component that provides an indication that the SUD should not be reused after exposure to elevated temperatures. FIGS. 5A and 5B illustrate one embodiment of a SUD 80 that utilizes a heat sensitive pop-up indicator 90 as a destruct element. The SUD 80 is again illustrated as a handle 82 that may support any of a variety of medical implements. In this embodiment, the pop-up indicator 90 is at least partially disposed in a recessed opening 86 formed in the proximal end of the handle 82. The pop-up indicator has a biasing pin 92 that includes a lower end disposed within the recessed opening and an upper end, which in the illustrated embodiment, is connected to a plate 96. The biasing pin also includes a central collar 94 having a cross-dimension (e.g., diameter) that is greater than the cross-dimension of the lower end of the pin 92. A biasing element 98 (e.g., coil spring), is disposed between the collar 94 and the bottom end of the recessed opening 86 of the handle 82. Prior to experiencing elevated temperatures, the lower end of the biasing pin 90 is disposed within a rigid potting material 100 and the biasing element is compressed between the collar and the bottom end of the recessed opening. The potting material 100 is made of a material having a low melting point (e.g., below an autoclaving temperature). Accordingly, upon being subjected to elevated temperatures during an autoclaving process, the potting material 100 softens or melts (e.g., deforms) releasing the lower end of the biasing pin 92. Once the potting material softens or melts, the compressed spring 98 expands and lifts the plate 96 above the proximal surface of the handle 82. As above, this provides a visual indication that the SUD should not be re-used. Though illustrated as being placed in the rearward end of the handle, it will be appreciated that the pop-up indicator could be placed at other locations including locations where a user grips the handle 82.

Figure 6A:
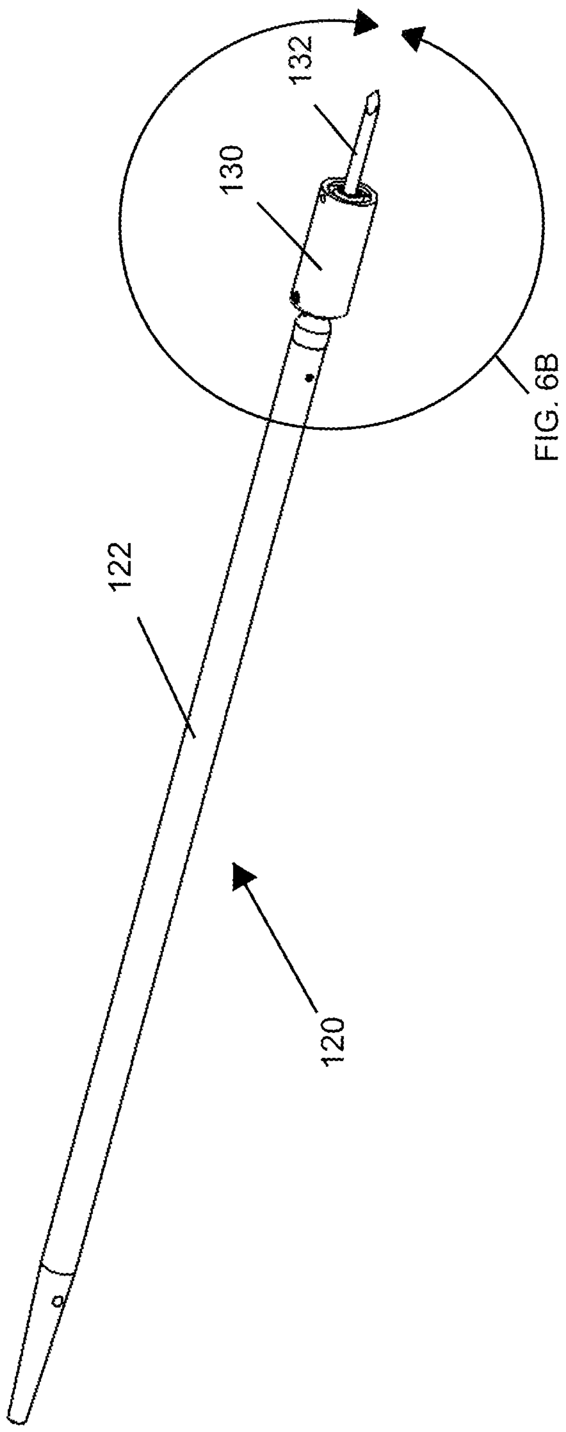
FIGS. 6A and 6B illustrate another single use medical device with a destruct element in accordance with the present disclosure.
Figure 6B:
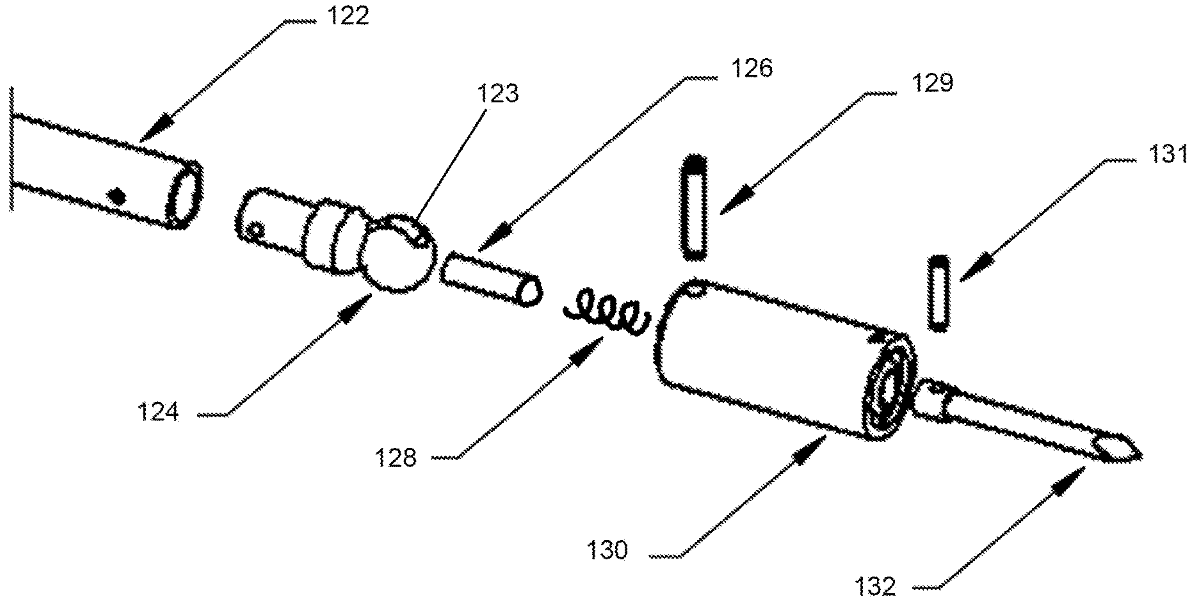

FIGS. 6A and 6B illustrate another SUD 120 in accordance with the present disclosure. In the illustrated embodiment, the SUD 120 is a medical awl having a moveable or swivel end. As illustrated, the SUD 120 includes a handle or shaft 122 a user may grasp to position an awl 132 connected to a forward or distal end of the shaft 122. As best illustrated in FIG. 6B, the awl 132 attaches to the shaft via a housing 130 that that engages a hemispherical ball 124 that is attachable to the distal end of the shaft 122. In the illustrated embodiment, the housing 130 is a generally cylindrical and at least partially hollow element that receives a rearward or proximal end of the awl 132 within its forward or distal end. A first pin 131 may be utilized to connect the awl 132 to the housing 130. Other connection mechanisms are possible. A rearward or proximal end of the housing 130 includes an opening (not shown) that is sized to receive the ball 124 connected to the distal end of the shaft 122. Once the ball 124 is disposed within the housing 130, a second pin 129 passes through the housing 130 and through an aperture 123 extending through the ball 124 to movably connect the housing 130 and awl 132 to the shaft 122.

The aperture 123 extending through the ball 124 is elongated, which allows the housing 130 and attached awl 132 to pivot about the end of the shaft 122 in at least first and second axes. A friction bearing 126 (hereafter "bearing") and spring 128 provide friction between the housing 130 and the ball 124. More specifically, when assembled, the spring 128 and a generally cylindrical bearing 126 are disposed within the housing 130 such that a proximal end of the bearing 126 is compressed against an outside surface of the ball 124 by the spring 128, which is itself compressed between a distal end of the bearing 126 and an inside surface (not shown) of the housing 130. Once assembled, the friction of the bearing 126 on the outside surface of the ball 124 provides resistance to movement, which allows positioning the awl 132 at a desired angle.

The bearing 126 is a thermally deformable destruct element in accordance with the present disclosure. That is, the bearing 126 has a low melting point of less than about 250° F., less than about 230° F. or even less than about 180° F. When subjected to autoclave processing temperatures, the bearing (e.g., destruct element) deforms or partially melts. Once the bearing 126 has sufficiently softened during an autoclave sanitation process, the spring 128 helps deform the bearing 126 by pushing it into the ball 124. In response to the pressure exerted by the spring 128, the bearing deforms into the functional swivel area (e.g., ball 124 and aperture 123, housing 130 and pin 129). Further, the spring 128 may become disposed within the distal end of the bearing 126. After an autoclaving process and the bearing material has re-solidifies (e.g., once cooled), the awl SUD 120 is inoperable. This is, due to the deformation of the bearing 126 during autoclaving into the functional swivel area, the housing 130 and awl 132 retain a fixed position relative to the shaft.

As noted above, the destruct elements are made of a material having a melting point that is less than a standard medical autoclaving temperature of approximately 121° C. or 250° F. A variety of materials may be utilized so long as those materials can be sterilized prior to the first use of a SUD (e.g., where such sterilization is by means other than elevated temperatures). Most commonly, the destruct material is a polymer. However, this is not a requirement. In one embodiment, the destruct material is Polycaprolactone (PCL), a biodegradable polyester with a low melting point of around 140° F. (60° C.). In another embodiment, paraffin wax may be utilized as the destruct material. Paraffin wax has a low melting point of approximately 154° F. In a further embodiment, the destruct material is a low-density polyethylene having a melting point of less that about 200° F. (90° C.). In a yet further embodiment, the destruct material is Polyethylene Glycol (PEG), which has a melting point of less than about 144° F. (62° C.). In various embodiments, the destruct material may be a material that acts similar to an adhesive when softened or melted. For example, various polymers may become sticky when softened/melted. Such materials tend to adhere to adjacent components when softened/melted. Once cooled (e.g., after autoclaving) such materials effectively bond to adjacent components thereby preventing movement of these components. Other materials are possible and considered within the scope of the present disclosure.

All directional references (e.g., distal, proximal, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A single use medical device, comprising:

a handle;

a medical implement attached to the handle; and a thermally deformable destruct element attached to the handle or the medical implement, wherein the thermally deformable destruct element is made of a material having a melting point of less than an autoclaving sterilization temperature, wherein the thermally deformable destruct element at least partially deforms when exposed to the autoclaving sterilization temperature; and a bias force element, wherein the thermally deformable destruct element at least partially biases the bias force element prior to the autoclaving process and wherein the bias force element at least partially expands when the thermally deformable destruct element is exposed to the autoclaving sterilization temperature thereby deforming the thermally deformable destruct element.

2. The single use medical device of claim 1, further comprising:

a movable part for moving the medical implement between a first position and a second position.

3. The single use medical device of claim 2, wherein a second thermally deformable destruct element is in direct contact with or forms a portion of the movable part, wherein deformation of the second thermally deformable destruct element prevents the movable part from moving between the first position and the second position.

4. The single use medical device of claim 2, further comprising:

at least a third thermally deformable destruct element made of a material having a melting point of less than the autoclaving sterilization temperature, wherein the third thermally deformable destruct element at least partially deforms when exposed to the autoclaving sterilization temperature and wherein the second thermally deformable destruct element and the third thermally deformable destruct element at least partially melt together when exposed to the autoclaving sterilization temperature.

5. The single use medical device of claim 1, wherein:

the bias force element is disposed in a recessed opening in the handle; and the thermally deformable destruct element is disposed over the recessed opening.

* * * * *